United States Patent [19]

Hamilton

[11] Patent Number: 4,571,188
[45] Date of Patent: Feb. 18, 1986

[54] OCCLUSAL MATRIX FOR LIGHT CURED COMPOSITES

[75] Inventor: James C. Hamilton, Ann Arbor, Mich.

[73] Assignee: Sybron Corporation, Rochester, N.Y.

[21] Appl. No.: 627,676

[22] Filed: Jul. 5, 1984

[51] Int. Cl.[4] .............................................. A61C 5/04
[52] U.S. Cl. ................................................. 433/226
[58] Field of Search ..................... 433/29, 39, 40, 228, 433/229, 215, 226

[56] References Cited

U.S. PATENT DOCUMENTS

| 3,949,477 | 4/1976 | Cohen | 433/24 |
| 4,445,858 | 5/1984 | Johnson | 433/229 |
| 4,449,928 | 5/1984 | Weissenfluh | 433/229 |

Primary Examiner—Robert Peshock
Attorney, Agent, or Firm—Robert A. Gerlach; Owen D. Marjama

[57] ABSTRACT

The disclosed invention is directed to a method of restoring a tooth with a light cured composite which comprises utilizing a light transparent impression or matrix which constitutes a negative reproduction of the occlusal surface of the tooth. The matrix is made by contacting the tooth surface with a polymeric impression material which when cured is light transparent and flexible. The polymeric impression material is allowed to set and then is stripped away from the tooth surface. A cavity preparation is then made in the tooth surface and treated in the usual manner. A light cured composite is then injected into the cavity preparation. The previously formed matrix is then placed over the light cured composite and pressure applied to the matrix. The composite is then cured by exposure to photopolymerizing light which passes through the transparent matrix. Following light curing, the matrix is stripped away from the tooth surface leaving a restored tooth with the original occlusal anatomy reproduced.

5 Claims, 8 Drawing Figures

OCCLUSAL MATRIX FOR LIGHT CURED COMPOSITES

BACKGROUND OF THE INVENTION

This invention relates to reproducing the original dental form in light-cured composites and is especially useful in placing posterior light-cured composites and forming the occlusal anatomy thereof. This invention also relates to a method of curing composite under light pressure and eliminating the air inhibited layer of present composites.

Dental practitioners have always attempted to reproduce the dental anatomy as it was before it was affected by disease (caries) or trauma. With chemically-cured dental composites, the dentist had limited working time. This limited the size of restorations that could be placed at one time and allowed little, if any, time for contouring. These restorations then require shaping after the material had sufficiently cured. This shaping and polishing is accomplished with rotary dental burs and finishing strips followed by a polishing paste.

With the advent of light-cured composites, the dental practitioner had much longer working time and therefore could shape the restoration more completely, but due to an air inhibited layer, still found it necessary to do a final shaping and polishing. This final shaping and polishing is even more complex on a posterior occlusal surface with the many grooves and sloping surfaces. This is compounded by the fact that the light-cured posterior composite restoration is similar in color to tooth structure and therefore, the exact finishing line between restorative material and tooth structure is difficult to visualize.

Also, on posterior teeth it has been noted that the proximal contact with composite material is more often deficient than with dental amalgam. This necessitated the checking of posterior contacts if approval was to be granted by the American Dental Association (Revised Guidelines for Submission of Composite Resin Material for Occlosal Class I and Class II Restorations).

Therefore, it is the objective of this invention to reproduce the original anatomy of the tooth being repaired with composite and at the same time, eliminate the air inhibited layer and allow for the composite to be cured under slight pressure which will reduce voids at the margin of the cavity preparation and help in establishing proximal contact of the final restoration.

SUMMARY OF THE INVENTION

The invention is directed to a method of restoring a tooth with a light cured composite which comprises utilizing a light transparent impression or matrix which constitutes a negative reproduction of the occlusal surface of the tooth. The matrix is made by contacting the tooth surface with a polymeric impression material which when cured is light transparent and flexible. The polymeric impression material is allowed to set and then is stripped away from the tooth surface. This article is called an occlusal matrix and constitutes an accurate negative reproduction of the occlusal surface of the tooth. A cavity preparation is then made in the tooth surface and treated in the usual manner. A light cured composite is then injected into the cavity preparation. The previously formed occlusal matrix is then placed over the light cured composite and pressure applied to the matrix. The composite is then cured by exposure to photopolymerizing light which passes through the transparent matrix. Following light curing, the matrix is stripped away from the tooth surface leaving a restored tooth with the original occlusal anatomy reproduced and no air inhibited layer which requires only limited final shaping and polishing. It should also be understood that the above technique is also useful placing a light-cured composite in a posterior or anterior tooth where the cavity or defect is on the facial or lingual surface, and also for veneering discolored teeth.

Figure 6:
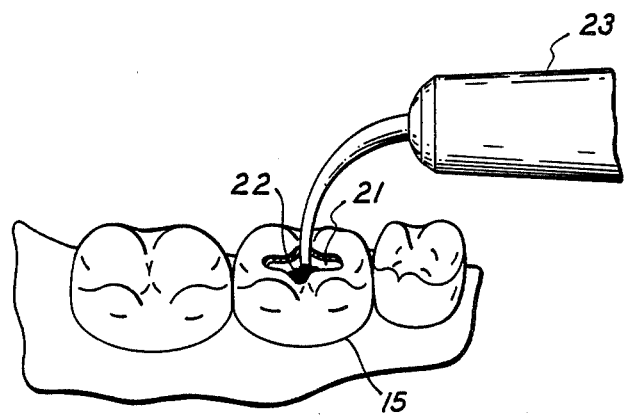

FIG. 6 illustrated filling a cavity preparation with a light curable dental composite.

Figure 4:
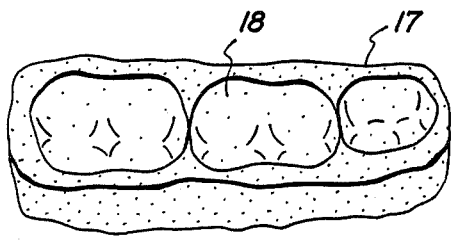
FIG. 4 is a perspective view of the matrix formed by the steps illustrated in FIGS. 2 and 3.
Figure 7:
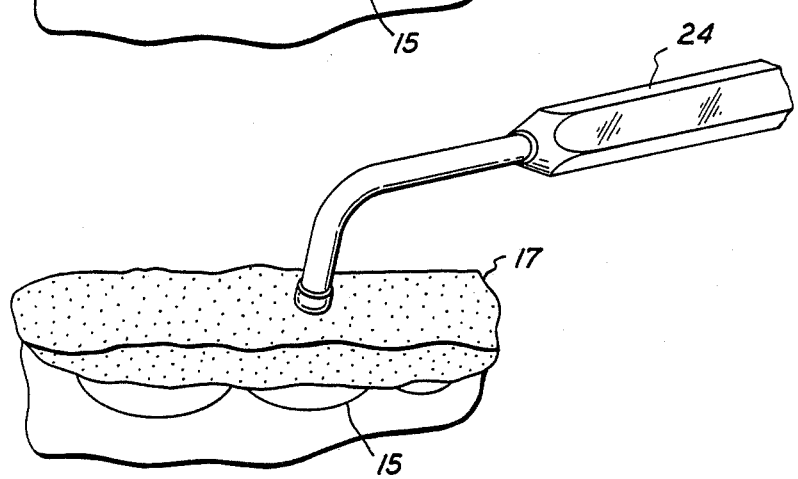

FIG. 7 illustrates using the occlusal matrix of FIG. 4 over the filled cavity preparation and curing the dental composite by exposure to a light curing bundle.

Figure 8:
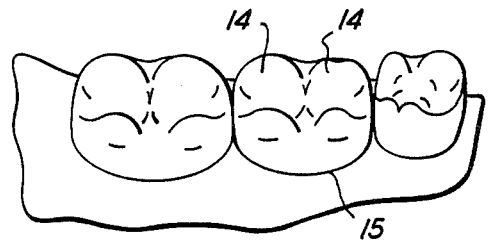

FIG. 8 illustrates the finished restored tooth.

DETAILED DESCRIPTION OF THE INVENTION

The material which comprises the occlusal matrix of the present invention can be any suitable chemically or light cured polymeric material which can form an accurate impression of a tooth-surface, and when set or cured is substantially light transparent and pliant or flexible.

A suitable material which may be used in carrying out the present invention is composed of the following:

| Base | | |
|---|---|---|
| 6% PS 123 | Polymethylhydro (65–70%)-dimethylsiloxane copolymer | |
| 94% PS 447.6 | Vinyldimethyl terminated polydimethylsiloxane 60,000 csk | |
| Catalyst | | |
| 1% PC 070 | Chloroplatinic acid complex | |
| 99% PS 447.6 | Vinyldimethyl terminated polydimethylsiloxane 60,000 csk | |

All components are available from Petrarch Systems, Inc. of Bristol, Pa. 19007.

Figure 1:
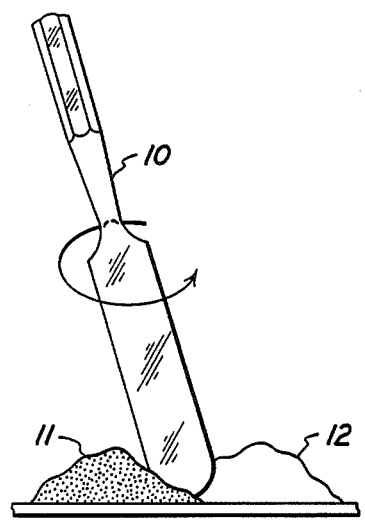
FIG. 1 illustrates the mixing of the ingredients which comprise the occlusal matrix material.
Figure 2:
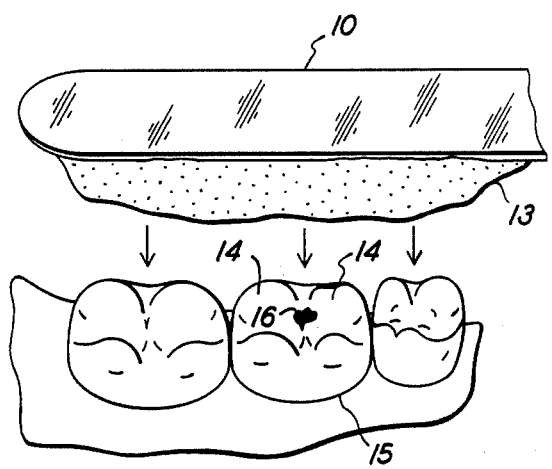
FIGS. 2 and 3 illustrate placing the matrix material on the tooth surface which is to be restored.
Figure 3:
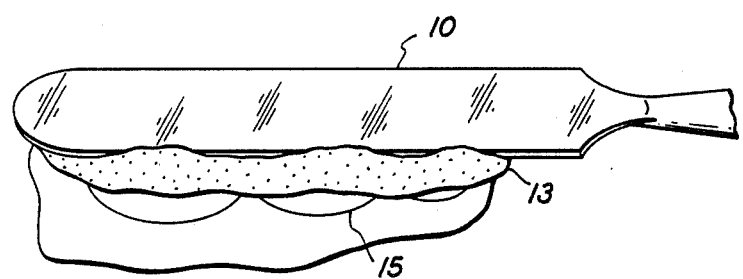

The following is an example of how this material would be used in placing a posterior occlusal light-cured composite restoration:

As illustrated by FIG. 1, the base 11 and catalyst 12 of the above noted formula are mixed together with a spatula 10 and a very thick, clear, syrup-like material 13 is formed. As shown in FIGS. 2 and 3, this material is placed on the occlusal surfaces 14 of a tooth 15 that is to be restored and the surrounding dental structure with the spatula and allowed to set (approximately 1½ minutes from start of mixing). In this case, tooth 15 contains a carious lesion which is illustrated by 16. When removed from the dental structure, an accurate negative reproduction 17 called an occlusal matrix is obtained as shown by FIG. 4. The occlusal matrix 17 constitutes an accurate negative reproduction 18 of the occlusal surface of tooth 15 which is to be restored along with the surrounding dental structure. The occlusal matrix must be transparent or substantially transparent in order to allow for a later applied photopolymorizing light to pass through it as will be discussed later.

Figure 5:
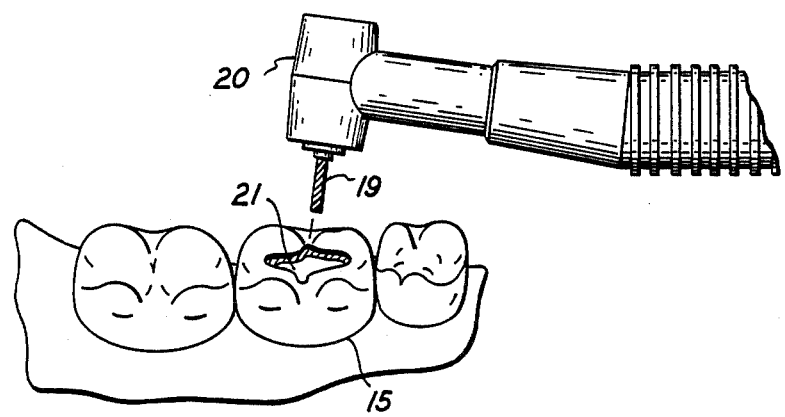
FIG. 5 illustrates the tooth preparation with a dental handpiece using a dental bur.

As illustrated in FIG. 5, the necessary tooth preparation is accomplished with a friction grip bur, 19 in a high-speed handpiece 20 resulting in the formation of cavity preparation 21. A calcium hydroxide cavity liner available and sold under the tradename "Life" by Sybron Corporation is placed on all exposed dentin within cavity preparation 21. The marginal enamel of the prepared tooth is etched with phosphoric acid (37–50% concentration) and then rinsed with warm water. Then the dental structure is dried. Light activated unfilled bonding resin is applied to the etched enamel and cured for 10 seconds. As shown by FIG. 6, a light-cured composite 22 is injected into the cavity preparation by syringe 23. This composite typically comprises a chemical composition which is a Bis GMA resin with a lower molecular weight monomer such as triethyleneglycol dimethocrylate to reduce viscosity combined with an inorganic filler. A photoinitiator such as camphoroquinone is used with a tertiary amine to start polymerization when exposed to visible light. These composites are available and sold under the tradenames Command Ultrafine by Kerr Division of Sybron Corporation and Silux by 3M Corporation. The previously made transparent, slightly flexible occlusal matrix 17 is placed over the cavity preparation which was previously filled with light-cured composite. Light finger pressure is applied to the occlusal matrix. This pressure is maintained with the operator end of the light curing bundle 24 (FIG. 7) and the occlusal surface is then cured with visible light for 20–30 seconds. Now the occlusal surface of the restoration is cured enough to allow for removal of the clear occlusal matrix. The restoration is cured further on the occlusal surface by placing the operator end of the fiberoptic light bundle directly on the occlusal surface and light curing for an additional length of time depending on the depth. A check is made for any excess composite material beyond the margins. If any excess composite is noted, this material is removed with a white polishing stone so as to make a flush margin. Because of the use of the transparent occlusal matrix, the majority of the occlusal anatomy is reproduced and does not need to be created by grinding the surface with a dental bur. Also, due to the lack of an air inhibited layer, the occlusal surface is also smooth and glossy as illustrated by FIG. 8. The occlusion is checked with articulating paper and any high spots are removed with a dental stone. Since the occlusal anatomy was reproduced as it originally was, there will be little need for adjusting the finished restoration.

The above technique is also useful placing a light-cured composite in an anterior tooth where the cavity or defect is on the facial or lingual surface as described below. Before the operative procedure is started, the base and catalyst are mixed to a clear, syrup-like consistency. This material is placed on the facial or lingual surfaces of the tooth being restored and the adjacent teeth. After setting approximately a minute and a half after the start of mix, this clear, flexible form is removed from the teeth. The cavity preparation is accomplished in the usual manner previously described above. A calcium hydroxide cavity liner such as "Life" is placed on all exposed dentin. The enamel margins of the cavity preparation are now etched with phosphoric acid, rinsed with warm water and dried with air from the air-water syringe. The bonding resin is applied to the etched enamel and cured with a visible light for 10 seconds. The light-cured composite is injected into the cavity preparation and the previously constructed clear, flexible matrix is placed on the facial or lingual surfaces of the teeth. By maintaining pressure on the flexible matrix with the operator end of the light bundle, the restoration is cured with visible light. After removing the clear, flexible matrix, the margins are checked for excess. Any excess is removed with white finishing stones and a dental handpiece.

In reproducing the contours of the labial surface when placing a full labial veneer with light cured composite, clear plastic matrix strips are placed adjacent to each tooth that is to be veneered. The base and catalyst pastes are mixed and placed on the labial surfaces incorporating the matrix strips. When set, the strips and set material is removed as a unit. The surfaces to be veneered are etched with acid, washed with water and dried with air. Separate matrix strips are placed interproximately adjacent to the tooth to be veneered. Light activated opaque or bonding resin is applied to the etched enamel and cured. Light activated dental composite is applied to the labial surface. The clear impression plus matrix strips are repositioned on the teeth being venerred and adjusted for the thickness of composite desired to be bonded to the labial surface. This technique is useful when veneering discolored teeth. The technique of the present invention may also be used in constructing full crown restorations.

Although particular embodiments of the present invention have been disclosed herein for purposes of explanation, further modifications or variations thereof will be apparent to those skilled in the art to which this invention pertains.

What is claimed is:

1. A method of restoring a tooth with a light cured composite which comprises:
    (a) forming a light transparent occlusal matrix which constitutes a negative reproduction of the occlusal surface of the tooth by contacting said tooth surface with a polymeric impression material which when cured is light transparent and flexible,
    (b) allowing the polymeric impression material to set and stripping it away from the tooth surface,
    (c) preparing a cavity preparation in the tooth surface,
    (d) injecting a light cured composite into the cavity preparation,
    (e) placing the previously formed occlusal matrix over said light cured composite and applying pressure to said matrix,
    (f) curing said composite by exposure to photopolymerizing light which passes through said transparent matrix,
    (g) followed by stripping said matrix away from the tooth surface.

2. A method of restoring a tooth with a light cured composite which comprises:
    (a) forming a light transparent facial matrix which constitutes a negative reproduction of the facial surface of the tooth by contacting said tooth surface with a polymeric impression material which when cured is light transparent and flexible,
    (b) allowing the polymeric impression material to set and stripping it away from the tooth surface,
    (c) preparing a cavity preparation in the tooth surface,
    (d) injecting a light cured composite into the cavity preparation, (e) placing the previously formed facial matrix over said light cured composite and applying pressure to said matrix, (f) curing said composite by exposure to photopolymerizing light which passes through said transparent matrix, (g) followed by stripping said matrix away from the tooth surface.

3. A method of restoring a tooth with a light cured composite which comprises:

(a) forming a light transparent lingual matrix which constitutes a negative reproduction of the lingual surface of the tooth by contacting said tooth surface with a polymeric impression material which when cured is light transparent and flexible, (b) allowing the polymeric impression material to set and stripping it away from the tooth surface, (c) preparing a cavity preparation in the tooth surface, (d) injecting a light cured composite into the cavity preparation, (e) placing the previously formed lingual matrix over said light cured composite and applying pressure to said matrix, (f) curing said composite by exposure to photopolymerizing light which passes through said transparent matrix, (g) followed by stripping said matrix away from the tooth surface.

4. A method of restoring a tooth with a full facial veneer with a light cured composite which comprises:

(a) forming a light transparent facial matrix which constitutes a negative reproduction of the facial surface of the tooth by contacting said tooth surface with a polymeric impression material which when cured is light transparent and flexible, (b) allowing the polymeric impression material to set and strip it away from the facial tooth surface, (c) etching the facial surface of the tooth with a dilute solution of phosphoric acid, (d) applying an opaquer or bonding agent to the etched surface and curing the opaquer to the surface to block out any discolored tooth structure, (e) placing a thin layer of light cured composite on top of the previously cured opaquer layer and applying the previously formed facial matrix over the tooth and applying light pressure to said matrix, (f) curing said composite by exposing to photo polymerizing light which passes through said transparent matrix, (g) followed by stripping said matrix away from the tooth's surface.

5. A method of restoring a tooth with a light cured composite which comprises:

(a) placing clear matrix strips on the mesial and distal surface of a tooth and then forming a light transparent matrix which covers the facial occlusal and lingual surfaces, and incorporating the two matrix strips of a tooth which is to be prepared for a crown, (b) allowing the polymeric impression material to set and stripping it away with the two matrix strips from the tooth surfaces, (c) preparing the tooth for a full crown, (d) injecting a light cured composite into the impression of the tooth before it was prepared for a full crown, (e) placing the previously formed matrix over said prepared tooth, (f) curing said composite by exposure to polymerizing light which passes through said transparent matrix, (g) followed by stripping away said transparent matrix and clear matrix strips from the tooth surfaces.

* * * * *